United States Patent [19]
Mizuta et al.

[11] Patent Number: 5,872,260
[45] Date of Patent: Feb. 16, 1999

[54] HIGH PURITY 1,3-DIALKYL-2-IMIDAZOLIDINONE AND PREPARATION PROCESS OF SAME

[75] Inventors: Hideki Mizuta, Fukuoka-ken; Masazumi Takaoka, Kumamoto-ken; Teruyuki Nagata, Fukuoka-ken, all of Japan

[73] Assignee: Mitsui Chemicals, Inc., Tokyo, Japan

[21] Appl. No.: 897,768

[22] Filed: Jul. 21, 1997

[30] Foreign Application Priority Data

Aug. 5, 1996 [JP] Japan .................................. 8-205692

[51] Int. Cl.$^6$ ................................................ C07D 233/32
[52] U.S. Cl. .......................................................... 548/316.4
[58] Field of Search ............................................ 548/316.4

[56] References Cited

U.S. PATENT DOCUMENTS 4,731,453  3/1988  Nagata et al. ........................... 548/317
4,897,480  1/1990  Schoenleben ........................... 548/317
5,011,936  4/1991  Kobayashi et al. ..................... 548/343
5,594,149  1/1997  Nause et al. .......................... 548/316.4

FOREIGN PATENT DOCUMENTS 0198345  10/1986  European Pat. Off. .
0248220  12/1987  European Pat. Off. .
0332425   9/1989  European Pat. Off. .

*Primary Examiner*—Patricia L. Morris
*Attorney, Agent, or Firm*—Burns, Doane, Swecker & Mathis, L.L.P.

[57] ABSTRACT

In a process for reacting N,N'-dialkylethylenediamine with urea in an aprotic polar solvent to prepare 1,3-dialkyl-2-imidazolidinone, a process comprising progressing the reaction while continuously adding N,N'-dialkylethylnediamine and urea into the aprotic polar solvent. The process is a high-yield manufacturing process in industry capable of efficiently producing very high purity 1,3-dialkyl-2-imidazolidinone which contains less than 0.1% by weight of by-product 1,3-dialkyl-2-imidazolidinimine derived from the raw materials.

6 Claims, 1 Drawing Sheet

HIGH PURITY 1,3-DIALKYL-2-IMIDAZOLIDINONE AND PREPARATION PROCESS OF SAME

BACKGROUND OF THE INVENTION

1. Field of the Invention

The present invention relates to 1,3-dialkyl-2-imidazolidinone and a preparation process of the same. More specifically, the invention relates to high-purity 1,3-dialkyl-2-imidazolidinone which can be obtained by reacting N,N'-dialkylethylenediamine with urea and has a very low content of a by-product, and a process for preparing the same.

1,3-Dialkyl-2-imidazolidinone is an aprotic solvent having high polarity, is very stable to acid and alkali compared with a conventional aprotic polar solvent, and has high dissolving power for various inorganic and organic compounds.

Thus, 1,3-dialkyl-2-imidazolidinone is a very useful compound as a solvent for preparing medicines, agricultural chemicals, dyestuffs and pigments, an agent for cleaning electronic parts and molds, and a solvent for polymerizing high polymer compounds.

2. Related Art of the Invention 1,3-Dialkyl-2-imidazolidinone has been conventionally prepared by a known process which reacts N,N'-dialkylethylenediamine with urea. The process was simple and excellent, but had a disadvantage of low yield. Later developments have improved the disadvantage.

U.S. Pat. No. 4,731,453 has disclosed a process for preparing 1,3-dialkyl-2-imidazolidinone in the yield of 80% or more by heating N,N'-dialkylethylenediamine and urea at temperature of 180° C. or more, preferably by previously completing the forming reaction of 1,1'-dimethyl-1,1'-dimethylenebisurea intermediate at 140° C. and successively reacting at temperature of 180° C. or more. However, according to the process, the product contains a by-product 1,3-dimethyl-2-imidazolidinimine in an amount of 0.5 to a few percents for 1,3-dimethyl-2-imidazolidinone. The by-product has a boiling point which is close to the boiling point of 1,3-dimethyl-2-imidazolidinone, and thus requires a column having a very high theoretical plate number in order to separate by distillation or a process for carrying out alternative treatment. Thus, the process of the U.S. Patent has problems in view of by-product removal.

When 1,3-dimethyl-2-imidazolidinone containing the by-product as above is used as a solvent, the by-product inhibits the desired reaction. For example, in the case of using as a solvent for preparing aramid, the by-product inhibits polymerization of the polymer.

Thus, 1,3-dimethyl-2-imidazolidinone has disadvantages in practical application.

However, the direct preparation process of 1,3-dialkyl-2-imidazolidinone from N,N'-dialkylethylenediamine and urea has merits of ①low material cost and ②no requirement for separating formed water as compared with conventionally known processes and is thus excellent as a process for manufacturing 1,3-dialkyl-2-imidazolidinone in an industrial scale. Consequently, the direct preparation process of 1,3-dialkyl-2-imidazolidinone in the absence of by-product formation has been strongly desired.

SUMMARY OF THE INVENTION

As a result of an intensive investigation in order to directly prepare high purity 1,3-dialkyl-2-imidazolidinone from N,N'-dialkylethylenediamine and urea in high yield, the present inventors have found that the above problem can be solved by the adoption of a method for progressing the reaction under a specific addition condition of the raw materials, that is, while continuously adding both raw materials into a hot aprotic polar solvent at the same time, and that 1,3-dialkyl-2-imidazolidinone can be very efficiently prepared with high yield in extremely high purity. Thus, the present invention has been completed.

That is, one aspect of the invention is:

① 1,3-Dialkyl-2-imidazolidinone having the formula (1):

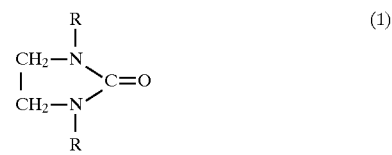

wherein R is an alkyl group, resulting from the reaction of N,N'-dialkylethylenediamine represented by the formula (2):

wherein R is an alkyl group, with urea, and containing less than 0.1% by weight of a by-product 1,3-dialkyl-2-imidazolidinimine represented by the formula (3):

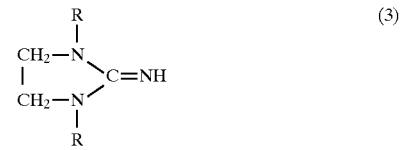

wherein R is an alkyl group; and

② A process for preparing 1,3-dialkyl-2-imidazolidinone represented by the formula (1) comprising reacting N,N'-dialkylethylenediamine with urea while continuously adding both raw materials to the aprotic polar solvent.

It is preferred in the process that:

1) Addition of N,N'-dialkylethylenediamine and urea is carried out so as to result in a residence time of 5 hours or more.

2) Reaction is progressed while continuously adding N,N'-dialkylethylenediamine and urea to an aprotic polar solvent maintained at a reaction temperature of 180° C. or more.

3) Reaction product is continuously discharged.

4) Reaction product 1,3-dialkyl-2-imidazolidinone is used as the reaction solvent.

5) R in the formulas is an alkyl group having 1 to 4 carbon atoms.

The present invention can provide 1,3-dialkyl-2-imidazolidinone being represented by the formula (1) and containing less than 0.1% by weight of the by-product 1,3-dialkyl-2-imidazolidineimine on manufacturing in industry by the reaction of N,N'-dialkylethylenediamine and urea. Further, the process of the invention can manufacture 1,3-dialkyl-2-imidazolidinone very efficiently in an industrial scale with good yield and extremely high purity. The process of the invention can also be carried out under atmospheric pressure and is thus greatly advantageous in view of manufacturing facility. Moreover, a continuous process enables more steady operation in an industrial scale and thus the invention has great significance.

Figure 1:
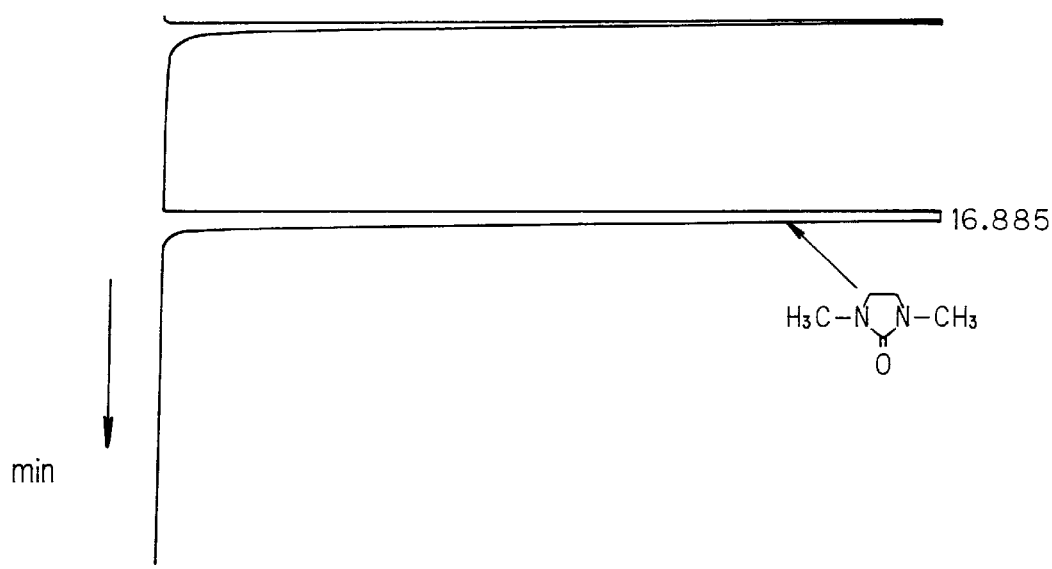
FIG. 1 shows a chart of gas chromatography of the 1,3-dimethyl-2-imidazolidinone of Example 1.

DETAILED DESCRIPTION OF THE INVENTION 1,3-Dialkyl-2-imidazolidinone in the invention is represented by the formula (1) and R is an alkyl group having 1 to 8 carbon atoms, 1 to 4 carbon atoms in particular. Specific compounds include 1,3-dimethyl-2-imidazolidinone, 1,3-diethyl-2-imidazolidinone, 1,3-dipropyl-2-imidazolidinone and 1,3-dibutyl-2-imidazolidinone. Particularly, 1,3-dimethyl-2-imidazolidinone is a useful compound and frequently used for various applications such as a solvent.

1,3-Dialkyl-2-imidazolidinone of the invention can be obtained by the reaction of N,N'-dialkylethylenediamine represented by the formula (2) and urea. In the reaction of these raw materials, the by-product 1,3-dialkyl-2-imidazolidinimine represented by the formula (3) is inevitably formed. In conventionally known processes, the amount of the by-product is 0.5% by weight or more for the product 1,3-dialkyl-2-imidazolidinone.

The content of the by-product 1,3-dialkyl-2-imidazolidinimine cannot be detected by chromatography in 1,3-dialkyl-2-imidazolidinone of the invention. The detection limit of 1,3-dialkyl-2-imidazolidinimine by chromatography is 0.1% by weight. Consequently, the content of the by-product is less than 0.1% by weight.

The process of the invention which can prepare high purity 1,3-dialkyl-2-imidazolidinone in high yield is characterized by progressing the reaction with continuous addition of N,N'-dialkylethylenediamine represented by the formula (2) and urea into the aprotic polar solvent.

Representative N,N'-dialkylethylenediamine which is represented by the formula (2) and can be used in the process of the invention includes the ethylenediamine which an alkyl group represented by R in the formula (2) has 1 to 8 carbon atoms, for example, N,N'-dimethylenediamine, N,N'-diethylethylenediamine, N,N'-dipropylethylenediamine, N,N'-diisopropylethylenediamine, N,N'-dibutylethylenediamine, N,N'-dibenzylethylenediamine, N,N'-dihexylethylenediamine, N,N'-diheptylethylenediamine and N,N'-octylethylenediamine.

In the above ethylenediamine, N,N'-dimethylethylenediamine, N,N'-diethylethylenediamine, N,N'-dipropylethylenediamine, N,N'-diisopropylethylenediamine and N,N'-dibutylethylenediamine are preferably used, N,N'-dimethylethylenediamine in particular. N,N-Dialkylethylenediamine corresponding to the desired 1,3-dialkyl-2-imidazolidinone is arbitrarily selected and used.

N,N'-Dialkylethylenediamine can be prepared with ease by reacting corresponding monoalkylamine with ethylene dihalide such as ethylene dichloride and ethylene dibromide.

The solvent which can be used in the process of the invention is an aprotic polar solvent. Desired effect cannot be provided satisfactorily by protic solvents such as water, alcohol and 2-oxoimidazolidine or aprotic low-polar solvents such as hydrocarbon and halogenated hydrocarbon. Thus, these solvents are unfavorable. However, these solvents can be used in admixture with aprotic polar solvents depending upon the object and reaction operation in the range not impairing the effect of the invention.

Preferred aprotic polar solvents which can be used in the process of the invention include N-methyl-2-pyrrolidone, N,N'-dimethylformamide, N,N'-dimethylacetamide, tetramethylurea, dimethylsulfoxide, hexamethylphosphoramide, sulfolane, dioxane and 1,3-dialkyl-2-imidazolidinone such as 1,3-dimethyl-2-imidazolidinone, 1,3-diethyl-2-imidazolidinone, and 1,3-dipropyl-2-imidazolidinone.

The reaction temperature is preferably 180° C. or more in the process of the invention. As a result, selected equipment is required when the solvent for use has a lower boiling point and a solvent having a boiling point of 180° C. or more is preferably used. Particularly, in view of avoiding complex operation for separating the solvent, 1,3-dialkyl-2-imidazolidinone which is formed by the reaction is most suitably used as intact for the solvent of a successive reaction.

In the process of the invention, the reaction temperature is preferably 180° C. or more, more preferably 200° to 260° C. When the reaction temperature is 180° C. or more, high reaction velocity can be obtained, residue of the intermediate 1,1'-dialkyl-1,1'-dimethylenebisurea can be avoided, and yield is increased. Reaction at higher temperature is also preferred in view of inhibiting formation of by-product such as 1,3-dialkyl-2-imidazolidinimine and other impurities. However, the reaction temperature is preferably 260° C. or less in consideration of a heating method in industry.

In the process of the invention, the reaction progresses while continuously adding N,N'-dialkylethylenediamine and urea to an aprotic polar solvent maintained at a reaction temperature of 180° C. or more.

Conventionally, it has been disclosed that 1,3-dialkyl-2-imidazolidinone can be prepared in high yield by previously reacting N,N'-dialkylethylenediamine with urea at lower temperature, completing the forming reaction of the intermediate 1,1'-dialkyl-1,1'-dimethylenebisurea, and successively heating to 180° C. or more to carry out a ring-closing reaction. However, the process could not inhibit formation of the by-product 1,3-dialkyl-2-imidazolidinimine. It has been quite impossible to anticipate that, as in the present invention, high purity 1,3-dialkyl-2-imidazolidinone having 0.1% by weight or less in the content of 1,3-dialkyl-2-imidazolidinimine by-product can be obtained in high yield by progressing the reaction with continuous addition of N,N'-dialkylethylenediamine and urea to an aprotic polar solvent maintained at 180° C. or more.

The ratio of N,N'-dialkylethylenediamine to urea which is used in the process of the invention is usually in the range of 1.0:0.5 to 1.0:2.0 by mole. The mole ratio in the range of 1.0:1.0 to 1.0:1.2 is most suited in order to reduce amount of by-product derived from N,N'-dialkylethylenediurea, to inhibit residual N,N'-dialkylethylenediamine and to prevent reduction of the yield.

No particular restriction is imposed upon the procedure for continuously adding N,N'-dialkylethylenediamine and urea in the invention. the continuous addition can be carried out (1) by previously mixing these materials and adding the resultant slurry, (2) by individually adding these two materials, or (3) by heat dissolving urea in an aprotic polar solvent and successively adding N,N'-dialkylethylenediamine. It is required to carry out continuous addition so as to immediately react N,N'- dialkylethylenediamine with urea in the aprotic polar solvent. The term "continuously" includes, when necessary, intermittent addition and continuous addition accompanied with change of addition velocity at a prescribed addition velocity over a prescribed time.

The speed for continuously adding required amounts of N,N'-dialkylethylenediamine and urea to the aprotic polar solvent in the process of the invention can be arbitrarily selected depending upon the kind of N,N'-dialkylethylenediamine and reaction temperature and no particular limitation is put upon the addition speed. However, the addition can be preferably carried out at a speed capable of substituting the whole amount of the aprotic polar solvent used during 5 hours or more, that is, a speed so as to obtain a residence time of 5 hours or more. A residence time of 5 to 10 hours is preferred in particular. For example, when 100 parts by weight of an aprotic polar solvent is used in the preparation of 1,3-dimethyl-2-imidazolidinone, a mixture of N,N'-dimethylethylenediamine and urea can be added at a speed capable of substituting 100 parts by weight of the aprotic polar solvent during 5 hours or more, that is, at a speed of 20 parts by weight/hour or less which results in a residence time of 5 hours or more. When added at a speed of less than 5 hours in the residence time, 1,1'-dimethyl-1,1'-dimethylenebisurea is liable to remain and reduce yield of 1,3-dialkyl-2-imidazolidinone.

Substantially no moisture content is preferable for N,N'-dialkylethylenediamine, urea and solvent such as 1,3-dialkyl-2-imidazolidinone which are used in the invention. When the reaction is carried out in a system containing no moisture, decomposition of urea in the course of the reaction and steam distillation of N,N'-dialkylethylenediamine out of the reaction system can be inhibited and reduction of yield can be prevented.

The temperature in the reaction is usually maintained constant.

The reaction can be carried out both at the atmospheric pressure and under increased pressure. The atmospheric pressure is usually adopted.

Continuous discharge of the reaction product enables steady operation. As a representative embodiment in this case, a reactor is equipped with inlet tubes of N,N'-dialkylethylenediamine and urea, respectively, and an outlet tube of the reaction product. An aprotic polar solvent is heated in the reactor and the reaction is progressed while continuously adding N,N'-dialkylethylenediamine and urea to the solvent. The formed 1,3-dialkyl-2-imidazolidinone is discharged from the outlet tube and preparation of 1,3-dialkyl-2-imidazolidinone can be continued for a long time. The reaction can be carried out both batch wise and continuously. The continuous method is desired in view of productivity and steady operation.

1,3-Dialkyl-2-imidazolidinone can be isolated with ease from the reaction product by distillation or other procedures.

The present invention will hereinafter be illustrated in detail by way of examples and comparative examples.

Analysis were carried out by gas chromatography. Purity of 1,3-dialkyl-2-imidazolidinone formed by the reaction of N,N'-dialkylethylenediamine and urea was analyzed by the method with a detection limit of 0.1% by weight of the by-product 1,3-dimethyl-2-imidazolidinimine.

In the Examples and Comparative Examples, the gas chromatograpy was carried out by the use of the following instruments;

Instrument: Shimazu GC-9A (Shimazu Seisakusho co.)

Column: 10% Uconoil 50HB 5100+5%Naoh Cromosorb WAW DMCS (GL Seientice co.)

Column temperature: 135° C.

Detector: Flame ionization detector (FID)

EXAMPLE 1

A discharge tube was installed on the bottom of a flask, and connected with a pump. A device for introducing into a 1 litre reactor was mounted on the discharge opening of the pump. A mixture of N,N'-dimethylethylenediamine and urea in a weight ratio of 57:43 was stirred in the flask.

To the 1 litre reactor, 100 g of 1,3-dimethyl-2-imidazolidinone (hereinafter referred to simply as DMI) was charged and maintained at 220° C. with stirring and successively the mixture of N,N'-dimethylethylenediamine and urea was added through the pump into the reactor at a speed of 20 g/hour. Addition was carried out over 30 hours while maintaining the internal temperature of the reactor at 215° to 220° C. After finishing the addition, stirring was further continued for 2 hours at the same temperature and the reaction mixture was cooled to room temperature.

The amount of the reaction mixture obtained was 542 g, the purity of DMI was 98.2% by weight, and 1,3-dimethyl-2-imidazolidinimine was not detected. The yield of DMI obtained by subtracting the amount of DMI initially charged to the reactor was 97.6% for N,N'-dimethylenediamine added.

Successively, the reaction mixture was distilled by using a distillation column having a theoretical plate number of 5 to obtain 506 g of DMI having purity of 99.9%. 1,3-Dimethyl-2-imidazolidinimine was not detected, that is, the content was less than 0.1%. FIG. 1 shows a chart of gas chromatography. As clearly shown in FIG. 1, presence of 1,3-dimethyl-2-imidazolidinimine is not found on the chart.

EXAMPLE 2

A discharge tube was installed on the bottom of a flask, and connected with a pump. A device for introducing into a 1 litre reactor was mounted on the discharge opening of the pump. The reactor was equipped on the body with a discharge tube, cooling tube and receiver. Internal content of the reactor including discharge portion was 600 ml.

To the reactor, 600 g of DMI was charged and maintained at 220° C. with stirring. Successively, a mixture of N,N'-dimethylethylenediamine and urea which was prepared at the same mixing ratio as Example 1 was added by the pump to the reactor at a speed of 100 g/hour. The addition was carried out over 24 hours while maintaining the internal temperature of the reactor at 215°~220° C. and storing the reaction product in the receiver.

After finishing addition, the reaction product was cooled. The amount of the reaction product in the reactor was 586 g. Purity of DMI was 98.1% by weight. DMI in the receiver was 1792 g and had a purity of 98.3% by weight. The whole amount of DMI in the reactor and receiver was 2337 g. The yield of DMI obtained by subtracting the amount of DMI which was initially charged to the reactor, was 97.7% for N,N'-dimethylethylenediamine. 1,3-Dimethyl-2-imidazolidinimine was not detected in the reaction product involved in the reactor and receiver. Chromatography had a detection limit of 0.1% and DMI reaction product had purity exceeding 99.9% by weight.

Successively, the liquid in the receiver was distilled by using a distillation column having a theoretical plate number of 5 to obtain 1691 g of DMI having purity exceeding 99.9% by weight (no detection of 1,3-dimethyl-2-imidazolidinimine).

EXAMPLE 3

To a reactor, 570 g of 1,3-dipropyl-2-imidazolidinone (hereinafter referred to simply as DPI) was charged.

To a flask, 1372 g of a mixture of N,N'-dipropylethylenediamine and 628 g of urea were charged and the same reaction procedures as described in Example 1 were carried out except that the addition speed of the mixture to the reactor was 70 g/hour.

The yield of DPI obtained by the same method as Example 1 was 97.2%. 1,3-Dipropyl-2-imidazolidinimine was not detected in the reaction product involved in the reactor and receiver. Chromatography had a detection limit of 0.1% and DPI reaction product had purity exceeding 99.9% by weight.

EXAMPLE 4

To a reactor, 600 g of N-methyl-2-pyrrolidone was charged.

To a flask, 2045 g of N,N'-dibutylethylenediamine and 856 g of urea were charged and mixed. The same reaction procedure as described in Example 1 were carried out except that the addition speed of the mixture to the reactor was 120 g/hour, and the internal temperature of the reactor was maintained at 200°~210° C.

The yield of 1,3-dibutyl-2-imidazolidinone obtained by the same method as Example 1 was 96.5%.

1,3-Dibutyl-2-imidazolidinimine was not detected in the reaction product involved in the reactor and receiver.

1,3-Dibutyl-2-imidazolidinone having purity exceeding 99.9% was thus obtained.

EXAMPLE 5

To the flask used in Example 1, 1140 g of urea and 2660 g of DMI were charged, urea was dissolved at 100° C. with stirring and maintained as intact. Another flask and pump were adopted and 1500 g of N,N'-dimethylethylenediamine was charged. To the reactor used in Example 1, 600 g of DMI was charged and the internal temperature was maintained at 220° C. Successively, the mixture of urea and DMI was added through the pump to the reactor at a speed of 150 g/hour, and at the same time N,N-dimethylethylenediamine was added to the reactor at speed of 60 g/hour. Addition time, reaction temperature and calculation method of yield were the same as Example 1.

The yield of DMI was 98.0%. 1.3-Dimethyl-2-imidazolidinimine was not detected in the reaction product involved in the reactor and receiver.

COMPARATIVE EXAMPLE 1

To a 500 ml autoclave, 88 g of N,N'-dimethylethylenediamine, 66 g of urea, and 100 g of DMI were charged, heated to 210° C. in 30 minutes, and reacted at the same temperature for 3 hours. Pressure of the reaction system was increased to a maximum of 15 kg/cm²G.

Figure 2:
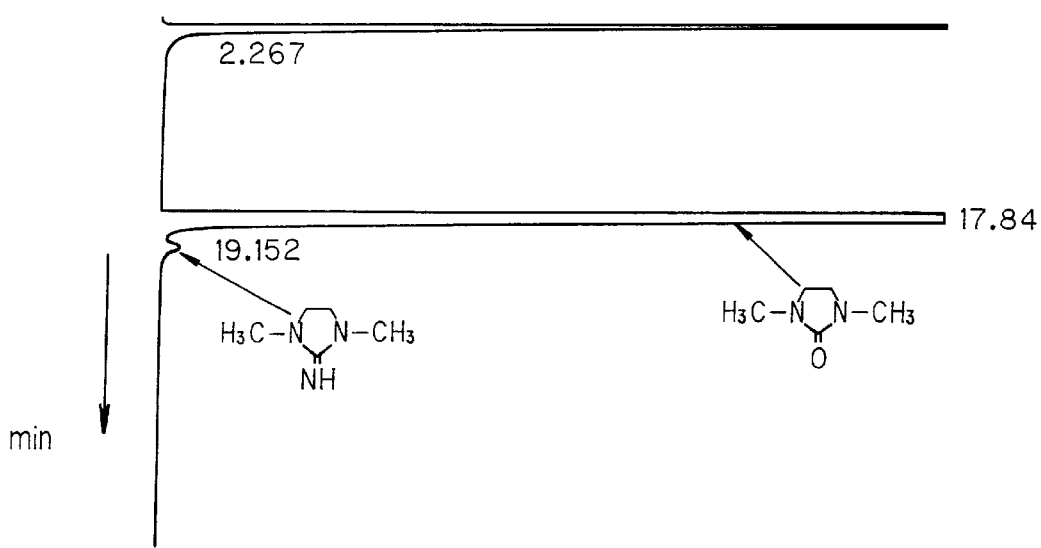
FIG. 2 shows a chart of gas chromatography of the 1,3-dimethyl-2-imidazolidinone of Comparative Example 1.

After finishing the reaction, the reaction mixture was discharged from the autoclave. A slurry containing white crystals was obtained. The slurry was filtered. The filtrate was DMI. DMI thus obtained was 200.1 g and had purity of 97.3% by weight. The yield of DMI obtained by subtracting the amount of DMI which was initially charged to the autoclave was 81.0% for N,N'-dimethylethylenediamine. In the filtrate, 0.8% by weight of 1,3-dimethyl-2-imidazolidinimine was detected. FIG. 2 illustrates a chart of gas chromatography.

Successively, the filtrate was distilled under the same conditions as Example 1. DMI thus obtained was 188 g and had purity of 99.2% by weight. The product was detected 0.7% by weight of 1,3-dimethyl-2-imidazolidinimine.

COMPARATIVE EXAMPLE 2

To the 500 ml autoclave, the same charge as Comparative Example 1 was carried out. The mixture was reacted at 120° C. for 8 hours. After initiating the reaction, the pressure in the system, gradually increased and became almost constant at 6 kg/cm²G. The temperature was successively increased to 210° C. in 30 minutes. The reaction was carried out 210° C. for 3 hours. The pressure in the system was increased to a maximum of 15 kg/cm²G.

The yield of DMI obtained by the same method as Comparative Example 1 was 96%. In the filtrate, 1.0% by weight of 1,3-dimethyl-2-imidazolidinimine was detected.

COMPARATIVE EXAMPLE 3

To a 300 ml flask equipped with a reflux condenser, dropping funnel and stirrer, 44 g of N,N'-dimethylethylenediamine, 66 g of urea and 100 g of DMI were charged, heated to 120° C. and reacted for 2 hours.

Successively, while increasing the temperature to 210° C., 44 g of N,N'-dimethylethylenediamine was charged to the dropping funnel and dropwise added from the temperature of 200° C. over 2 hours. The reaction was further carried out at 215° to 220° C. for one hour.

The yield of DMI obtained by the same method as Comparative Example 1 was 97.0%. In the filtrate, 0.5% by weight of 1,3-dimethyl-2-imidazolidinimine was detected.

That is, Comparative Examples 1 to 3 which were outside the scope of the invention generated 1,3-dialkyl-imidazolidinimine having a boiling point close to the boiling point of 1,3-dialkyl-2-imidazolidinone.

On the other hand, according to the invention as shown in Examples 1 to 5, high purity 1,3-dialkyl-2-imidazolidinone could be obtained with ease in good efficiency and high yield in the absence of 1,3-dialkyl-2-imidazolidinone generation.

What is claimed is:

1. In a process for reacting N,N'-dialkylethylenediamine represented by the formula (2):

wherein R is an alkyl group, with urea in an aprotic solvent at a temperature of 180° C. or more to prepare 1,3-dialkyl-2-imidazolidinone represented by the formula (1):

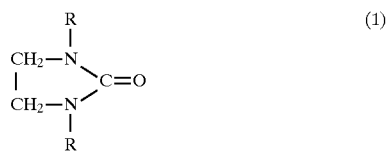

wherein R is an alkyl group, the process comprising conducting the reaction while continuously adding N,N'-dialkylethylenediamine represented by the formula (2) and urea to the aprotic polar solvent.

2. A preparation process according to claim 1 wherein R in the formulas (1) and (2) is an alkyl group having 1 to 4 carbon atoms.

3. A preparation process according to claim 1 wherein the aprotic polar solvent is 1,3-dialkyl-2-imidazolidinone.

4. A preparation process according to claim 1 wherein the addition of N,N'-dialkylethylenediamine and urea is carried out at a speed so as to obtain a residence time of 5 hours or more.

5. A preparation process according to claim 1 wherein reaction product is continuously discharged from the reaction system.

6. A preparation process according to claim 1 wherein the 1,3-dialkyl-2-imidazolidinone prepared by the process has less than 0.1% by weight of 1,3-dialkyl-2-imidazolidinimine represented by formula (3)

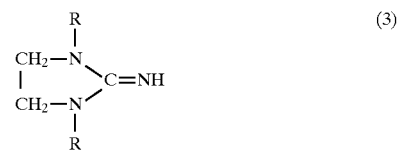

wherein R is an alkyl group.

* * * * *